(12) United States Patent
Wang (10) Patent No.: US 12,390,806 B2
(45) Date of Patent: Aug. 19, 2025

(54) CENTRIFUGAL REACTION MICROTUBE, CENTRIFUGAL REACTION DEVICE AND ITS CENTRIFUGAL EXAMINATION METHOD

(71) Applicant: Chin Hung Wang, Taipei (TW)

(72) Inventor: Chin Hung Wang, Taipei (TW)

( * ) Notice: Subject to any disclaimer, the term of this patent is extended or adjusted under 35 U.S.C. 154(b) by 923 days.

(21) Appl. No.: 17/616,104

(22) PCT Filed: Jun. 13, 2019

(86) PCT No.: PCT/CN2019/091171
§ 371 (c)(1),
(2) Date: Dec. 2, 2021

(87) PCT Pub. No.: WO2020/248203
PCT Pub. Date: Dec. 17, 2020

(65) Prior Publication Data
US 2022/0314214 A1    Oct. 6, 2022

(51) Int. Cl.
| | | |
|---|---|---|
| *B01L 3/00* | (2006.01) | |
| *B01J 19/00* | (2006.01) | |
| *C12Q 1/68* | (2018.01) | |
| *G01N 21/75* | (2006.01) | |

(52) U.S. Cl.
CPC ......... *B01L 3/5021* (2013.01); *B01J 19/0046* (2013.01); *C12Q 1/68* (2013.01); *B01J 2219/00722* (2013.01); *B01L 2300/087* (2013.01); *B01L 2400/0409* (2013.01);
(Continued)

(58) Field of Classification Search
CPC ......... B01J 19/0046; B01J 2219/00722; B01L 2200/0621; B01L 2300/0864; B01L 2300/087; B01L 2400/0409; B01L 2400/0605; B01L 2400/0633; B01L 3/5021; C12Q 1/68; G01N 21/75
See application file for complete search history.

(56) References Cited

U.S. PATENT DOCUMENTS 8,480,980 B2   7/2013 Yoo
2002/0151078 A1* 10/2002 Kellogg ............... B01L 3/5027
                                                    436/180
(Continued)

FOREIGN PATENT DOCUMENTS

CN    1477400    2/2004
CN    103041882  4/2013
(Continued)

OTHER PUBLICATIONS

KR2015-013462A English translation (Year: 2024).*
(Continued)

*Primary Examiner* — Jennifer Wecker
*Assistant Examiner* — Jonathan Bortoli
(74) *Attorney, Agent, or Firm* — Branch Partners PLLC; Bruce E. Black (57) ABSTRACT

A centrifugal reaction microtube, centrifugal reaction device and its centrifugal examination method are provided to achieve easy, quick operation, safety, energy saving, precision, cost effectiveness, and prevention of contamination by controlling a centrifugal force and using a uni-directional valve in the centrifugal reaction microtube.

25 Claims, 9 Drawing Sheets

(52) U.S. Cl.
CPC ................. *B01L 2400/0605* (2013.01); *B01L 2400/0633* (2013.01); *G01N 21/75* (2013.01)

(56) References Cited

U.S. PATENT DOCUMENTS

| | | | |
|---|---|---|---|
| 2005/0221281 A1* | 10/2005 | Ho | .............. G01N 21/6452 |
| | | | 435/287.1 |
| 2006/0116270 A1 | 6/2006 | Hatamian et al. | |
| 2006/0133957 A1 | 6/2006 | Knapp et al. | |
| 2013/0171697 A1* | 7/2013 | Park | .................. C12N 1/08 |
| | | | 536/25.41 |
| 2014/0370499 A1 | 12/2014 | Hoang et al. | |
| 2016/0102673 A1* | 4/2016 | Cherry | ............... F04D 17/18 |
| | | | 417/54 |
| 2017/0036208 A1* | 2/2017 | Veres | ............. B01L 3/502715 |
| 2018/0038854 A1* | 2/2018 | Choi | ................... G01N 35/00 |
| 2018/0147340 A1* | 5/2018 | Vidal Fayos | ....... A61M 1/3696 |
| 2018/0161772 A1* | 6/2018 | Rammohan | ...... G01N 33/54313 |

FOREIGN PATENT DOCUMENTS

| | | | | |
|---|---|---|---|---|
| CN | 104535514 | | 4/2015 | |
| CN | 206810314 | | 12/2017 | |
| CN | 108449996 | | 8/2018 | |
| KR | 2015013462 A | * | 2/2015 | ............ G09B 23/00 |
| KR | 20150134562 | | 12/2015 | |
| TW | 468040 | | 12/2001 | |
| TW | I245073 | | 12/2005 | |
| TW | I360438 | | 3/2012 | |
| WO | WO2014086912 A1 | | 6/2014 | |

OTHER PUBLICATIONS

International Search Report for PCT Application No. PCT/CN2019/091171 mailed Mar. 12, 2020.
Written Opinion for PCT Application No. PCT/CN2019/091171 mailed Mar. 12, 2020.
International Preliminary Report on Patentability for PCT Application No. PCT/CN2019/091171 mailed Dec. 23, 2021.
Extended European Search Report for EP Patent Application No. 19932490.6 mailed May 4, 2023.

* cited by examiner

CENTRIFUGAL REACTION MICROTUBE, CENTRIFUGAL REACTION DEVICE AND ITS CENTRIFUGAL EXAMINATION METHOD

CROSS-REFERENCE TO RELATED APPLICATIONS

This present application is a U.S. national stage application of PCT Application No. PCT/CN2019/091171, filed Jun. 13, 2019, which is hereby incorporated by reference in its entirety.

BACKGROUND OF THE INVENTION

Field of the Invention

The present disclosure relates to experiment-oriented reaction microtubes and reaction devices and, more particularly, to a reaction microtube and reaction device capable of performing molecular biological testing with one click.

Description of the Prior Art

Owing to biological technology advancement, there is increasingly great demand for conducting testing with biochemical and molecular biological methods. Although there are existing commercially-available polymerase chain reaction (PCR) instruments for performing nucleic acid sequence-based amplification and analysis simultaneously, they have to operate in conjunction with the other instruments, such as electric pipette, nucleic acid hybridizator, rinser, and signal interpretative instrument, in order to perform all the testing steps. Therefore, not only is the testing process usually complicated and time-consuming, but the liquid transport process is also predisposed to contamination.

When the nucleic acid or specimen to be analyzed is extremely complicated, existing commercially-available products can neither perform the entire molecular biological testing with one click nor simultaneously carry out qualitative analysis and quantitative analysis.

SUMMARY OF THE INVENTION

In view of the aforesaid drawbacks of the prior art, it is an objective of the present disclosure to provide a centrifugal reaction microtube and a reaction device. Through the design of the reaction microtube, it is feasible for extraction, reaction, rinsing and/or signal detection to take place in the same reaction microtube by carrying out centrifugation, thereby reducing contamination and demand for manpower.

In order to achieve the above and other objectives, the present disclosure provides a centrifugal reaction microtube, comprising:
  a first reaction area for containing a reaction mixture to undergo a first reaction; and
  a first uni-directional valve located in a centrifugation direction of the first reaction area and opened under a first centrifugal force to allow the reaction mixture to exit the first reaction area.

Preferably, the centrifugal reaction microtube further comprises;
  a second reaction area separated from the first reaction area by the first uni-directional valve, wherein the reaction mixture moves to the second reaction area under the first centrifugal force to undergo a second reaction; and
  a second uni-directional valve disposed on a side opposite to the first uni-directional valve in the second reaction area, and opened under a second centrifugal force to allow the reaction mixture to exit the second reaction area.

Preferably, the second centrifugal force is greater than the first centrifugal force.

Preferably, the first centrifugal force and the second centrifugal force may range from 1 g to 80,000 g, and the second centrifugal force is greater than the first centrifugal force.

Preferably, the first uni-directional valve and the second uni-directional valve may be opened and shut by electrical control or magnetic control.

Preferably, the centrifugal reaction microtube may further comprises a biochip disposed in the second reaction area and coated with biological molecules including an antibody, an aptamer, a peptide or a nucleic acid.

Preferably, the centrifugal reaction microtube may further comprises a liquid waste area separated from the second reaction area by the second uni-directional valve.

Preferably, the first reaction area may undergo a polymerase chain reaction, and/or the second reaction area may undergo a nucleic acid hybridization.

Preferably, the centrifugal reaction microtube further comprises:
  a third reaction area for containing the reaction mixture to undergo a third reaction; and
  a third uni-directional valve disposed between the third reaction area and the first reaction area, allowing the reaction mixture to move to the first reaction area under a third centrifugal force.

Preferably, the centrifugal reaction microtube may be substantially made of an optical material. Preferably, the optical material may be quartz, glass or plastic.

According to another objective of the present disclosure, an embodiment of the present disclosure further provides a centrifugal reaction device comprising a reaction centrifugal disk tilting upward at a slope from an axle and having a plurality of holders arranged symmetrically and adapted to receive a plurality of said centrifugal reaction microtubes.

Preferably, the slope may ranges from about 1° to 89°.

Preferably, the centrifugal reaction device may further comprises a signal detector for detecting a reaction signal of the centrifugal reaction microtubes.

Preferably, the centrifugal reaction device may further comprises a liquid dispenser for introducing a reaction reagent and/or a specimen into the centrifugal reaction microtubes, respectively.

Preferably, the centrifugal reaction device may further comprises a temperature controller for controlling a reaction temperature of the centrifugal reaction microtubes.

Preferably, the centrifugal reaction device may further comprises a liquid waste collector for collecting a liquid waste having exited the centrifugal reaction microtubes.

According to still another objective of the present disclosure, an embodiment of the present disclosure further provides a centrifugation examination method, comprising the steps of:
  providing the centrifugal reaction microtube; and
  introducing a specimen and/or a reaction reagent into the first reaction area to form a reaction mixture for undergoing a first reaction by centrifuging the centrifugal reaction microtube.

Preferably, the method may further comprises the step of introducing a rinsing solution and intermittently centrifuging the centrifugal reaction microtube.

Preferably, the method may further comprises the step of detecting a reaction signal of the centrifugal reaction microtube.

Preferably, the method may further comprises the step of controlling a reaction temperature of the centrifugal reaction microtube.

Preferably, the method may further comprises the step of collecting a liquid waste having exited the centrifugal reaction microtube.

Preferably, the method may further comprises the step of centrifuging the centrifugal reaction microtube and moving the reaction mixture through the first uni-directional valve to a second reaction area so as to undergo a second reaction, under a first centrifugal force.

Preferably, the method may further comprises the step of centrifuging the centrifugal reaction microtube and moving the reaction mixture through a second uni-directional valve away from the second reaction area, under a second centrifugal force uni-directional.

Preferably, the second centrifugal force is greater than the first centrifugal force.

Preferably, the first centrifugal force and the second centrifugal force may range from 1 g to 80,000 g, and the second centrifugal force is greater than the first centrifugal force.

Preferably, the first uni-directional valve and the second uni-directional valve may be opened and shut by electrical control or magnetic control.

Preferably, the first reaction area may undergo a polymerase chain reaction, and/or the second reaction area may undergo nucleic acid hybridization.

The above and other objectives, features, and advantages of the present disclosure are hereunder illustrated with preferred embodiments, depicted with accompanying drawings, and described below.

BRIEF DESCRIPTION OF THE DRAWINGS

The description below is full of specific details to explain the present disclosure and illustrate the embodiments of the present disclosure. However, obviously, one or more embodiments can be implemented in the absence of the specific details. In the other circumstances, conventional structures and process flows are schematically shown in the accompanying drawings in order to simplify the accompanying drawings.

DETAILED DESCRIPTION OF THE EMBODIMENTS

The present disclosure is depicted by the accompanying drawings, illustrated by embodiments, and described below. The embodiments are implemented in different forms which, however, are not necessarily required to implement or apply the present disclosure. Thus, the different forms of implementation must not be interpreted in a way to limit the embodiments. Features of specific embodiments, steps of a method for constructing and operating specific embodiments, and the sequence of the steps of the method are disclosed hereunder. However, it is also feasible to use any other specific embodiments to achieve identical or equivalent functions and step sequence. Conversely, the embodiments are provided, such that the description hereunder can be thoroughly and completely presented to sufficiently inform persons skilled in the art of the spirit of the present disclosure. Similar reference numerals used in the accompanying drawings denote similar components. Conventional functions or structures are omitted from the description below for the sake of brevity.

Unless otherwise defined, all the technical terms and jargons used hereunder shall have the same meanings as normally understood by persons skilled in the art. If there is any inconsistency between this specification and the comprehension of persons skilled in the art, the definitions-containing specification shall prevail.

Each singular noun used hereunder includes the plural form of the noun without contradicting the context. Each plural noun used hereunder includes the singular form of the noun without contradicting the context. Furthermore, the expression "at least one" and the expression "one or more" used hereunder have the same meaning, and both include one, two, three or more.

The expression "consisting essentially of" used hereunder is for use in defining a composition, method or device, including any materials, steps, features, constituents or components other than what are expressly stipulated. Its restrictive criterion is: the additional materials, steps, features, constituents or components do not significantly affect essential and novel features of an invention claimed. The scope of the expression "consisting essentially of" lies between that of the expression "comprising" and that of the expression "consisting of".

The relatively broad scope of the present disclosure is defined by numerical ranges and parameters which are approximate for general description. Furthermore, the numerical ranges and parameters inevitably come with standard deviations associated with any examination methods. The aforesaid "about" means that an actual value can be 10%, 5%, 1% or 0.5% greater than or less than a specific value or a limit of a range. Alternatively, the aforesaid "about" means that an actual value falls within an acceptable standard deviation of its mean, depending on the considerations which persons skilled in the art take into account. In addition to the embodiments of the present disclosure, or unless otherwise expressly specified, all the ranges, numbers, numerical values, and percentages (for example, descriptive of the amount of a material in use, a period of time, temperature, operation conditions, numeric proportions, and the like) stated hereunder are each followed by the adverb "about". Therefore, unless otherwise conversely specified, all the numerical ranges and parameters disclosed hereunder are presented in the form of approximate numerical values and are subject to changes as needed. The numerical values and parameters must be at least interpreted to be applicable to significant figures and general decimal notation. The ranges of the numeral values are each defined with an endpoint and another endpoint or defined as a range between two endpoints. Unless otherwise specified, the ranges of the numeral values disclosed hereunder include their respective endpoints.

In an embodiment, providing a centrifugal reaction microtube which comprises: at least one reaction area for containing a reaction mixture including a reaction reagent, rinsing solution and/or specimen to undergo a reaction; and at least one uni-directional valve disposed in a centrifugation direction of the reaction area. The reaction mixture flows under the centrifugal force in a direction away from the axle. When the centrifugal speed or centrifugal force exceeds a threshold, the uni-directional valve opens, allowing the reaction mixture to exit from the reaction area. When the centrifugal speed or centrifugal force is lower than a threshold, the uni-directional valve shuts, preventing the reaction mixture from flowing back to the original reaction area. Thus, by opening or shutting the uni-directional valve repeatedly and selectively, it is feasible to partition the reaction microtube area into at least one reaction area for purification, amplification and analysis of any substances (biological molecules, such as proteins and nucleic acids) to be analyzed.

The "uni-directional valve" disclosed hereunder may control a reaction reagent, rinsing solution and/or specimen to stay within a reaction area before centrifugation and may cause, upon centrifugation, the reaction reagent, rinsing solution and/or specimen to flow in uni-direction to another reaction area via the "uni-directional valve" but not to flow back.

The operating principle of the uni-directional valve may come in different ways. For example, a mechanical uni-directional valve comprises springs with different elastic moduli and balls of different weights and may be made of metal or nonmetal. Different magnitudes of centrifugal forces may correspond to valves with different elastic moduli work, such that different valves in the reaction microtube open or shut under different magnitudes of centrifugal forces. Thus, the uni-directional valve effectuates the retention or discharge of the reaction mixture, depending on whether the magnitude of the centrifugal force is high or low. In addition, a uni-directional valve can also be electrically-controlled or magnetically-controlled so as to be opened and shut.

For instance, when the opening and shutting of the uni-directional valve is controlled with a compression spring, as the compression spring is provided stationary, centrifugation has not begun, or the centrifugal force has not reached the compression stress of the spring, the compression spring will be completely stretched, and the uni-directional valve will be completely hermetically sealed. When the centrifugal force reaches the compression stress of the spring, the gradual increase in the magnitude of the centrifugal force causes the compression spring to shorten gradually because of compression and thus causes the uni-directional valve to open, allowing the reaction mixture to move away from the direction of rotating the axle to thereby pass through the uni-directional valve.

All the liquid waste produced in the course of a reaction may be collected in a sealed manner or in vacuum, depending on whether the reaction microtube has an opening and according to the amount of the liquid waste. In an embodiment, the liquid waste is collected in a sealed manner, and the centrifugal reaction microtube may further comprises a liquid waste area. Owing to the separation of the uni-directional valve to the liquid waste area and the reaction area, the rinsing solution or reaction mixture which has undergone the reaction in the reaction area can leave the reaction area to the liquid waste area by centrifugation and thus does not flow back.

In an embodiment, a biochip may be disposed in the reaction area of the centrifugal reaction microtube and coated with biological molecules in order to undergo hybridization with the reaction mixture. The biological molecules may include antibodies, aptamers, peptides or nucleic acids.

Figure 1:
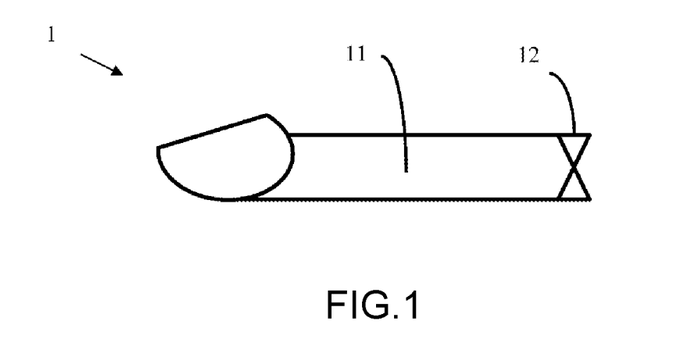
FIG. 1 is a schematic view of a centrifugal reaction microtube according to embodiment 1 of the present disclosure.

As shown in FIG. 1, in the first embodiment, a centrifugal reaction microtube 1 comprises a reaction area 11 and a uni-directional valve 12. For instance, after undergoing PCR amplification, nucleic acid molecules may react with a biochip pre-coated with target nucleic acids in the reaction area 11. Then, partially complementary nucleic acid molecules are attached to the biochip. Next, upon centrifugation, unattached nucleic acid molecules are removed through the uni-directional valve 12.

Figure 2:
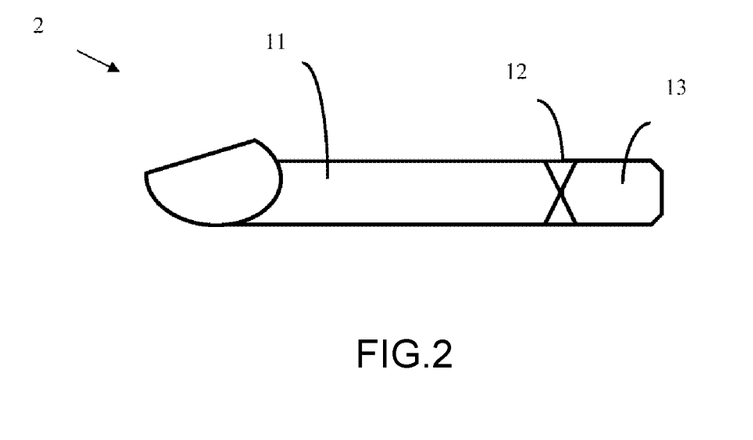
FIG. 2 is a schematic view of the centrifugal reaction microtube according to embodiment 2 of the present disclosure.

In embodiment 2, as shown in FIG. 2, a centrifugal reaction microtube 2 not only includes a reaction area 11 and a uni-directional valve 12 but also comprises a liquid waste area 13 for collecting a liquid waste after the reaction.

Figure 3:
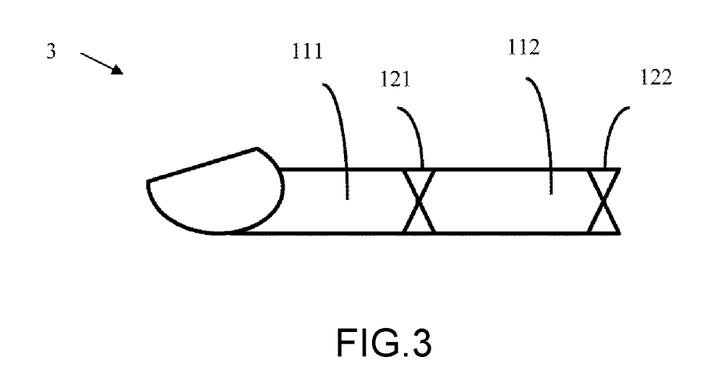
FIG. 3 is a schematic view of the centrifugal reaction microtube according to embodiment 3 of the present disclosure.

In embodiment 3, as shown in FIG. 3, a centrifugal reaction microtube 3 comprises a first reaction area 111, first uni-directional valve 121, second reaction area 112 and second uni-directional valve 122. The first reaction area 111 may be used for undergoing the first reaction of the reaction mixture. The first uni-directional valve 121 is disposed in the centrifugation direction of the first reaction area 111. The second reaction area 112 and the first reaction area 111 are separated by the first uni-directional valve 121. The second uni-directional valve 122 is disposed at an opposite side to the first uni-directional valve 121 in the second reaction area 112.

In embodiment 3, given the two reaction areas, two reactions can be sequentially carried out in the same centrifugal reaction microtube 3. For instance, the first reaction area 111 may undergo a polymerase chain reaction, and/or the second reaction area 112 may undergo nucleic acid hybridization. Alternatively, the first reaction area 111 may undergo nucleic acid extraction, and/or the second reaction area 112 may undergo nucleic acid hybridization.

In this embodiment, persons skilled in the art choose springs with different or equal elastic moduli as needed, so as to control the opening and shutting of the first uni-directional valve 121 and second uni-directional valve 122 under the same or different centrifugation conditions. In a preferred embodiment, when springs with equal elastic moduli are in use, the springs operate in conjunction with balls of different weights, by positioning heavy balls at the first uni-directional valve 121 and light balls at the second uni-directional valve 122. Thus, the centrifugal force under which the first uni-directional valve 121 opens is less than the centrifugal force under which the second uni-directional valve 122 opens. Therefore, at low rotation speed, only the first uni-directional valve 121 opens, but the second uni-directional valve 122 shuts. In another preferred embodiment, when springs with different elastic moduli are in use, the elastic moduli of the springs of the second uni-directional valve 122 are greater than the elastic moduli of the springs of the first uni-directional valve 121 to prevent the reaction mixture in the first reaction area 111 from passing through the first uni-directional valve 121 and second uni-directional valve 122 upon centrifugation rather than staying in the second reaction area 112. In this situation, the centrifugal force under which the second uni-directional valve 122 opens is greater than the centrifugal force under which the first uni-directional valve 121 opens, and thus the second uni-directional valve 122 can open only at a high rotation speed. Therefore, at a low rotation speed, only the first uni-directional valve 121 opens, but the second uni-directional valve 122 shuts.

In a preferred embodiment, the first centrifugal force and the second centrifugal force may range from 1 g to 80,000 g, and the second centrifugal force is greater than the first centrifugal force.

Figure 4:
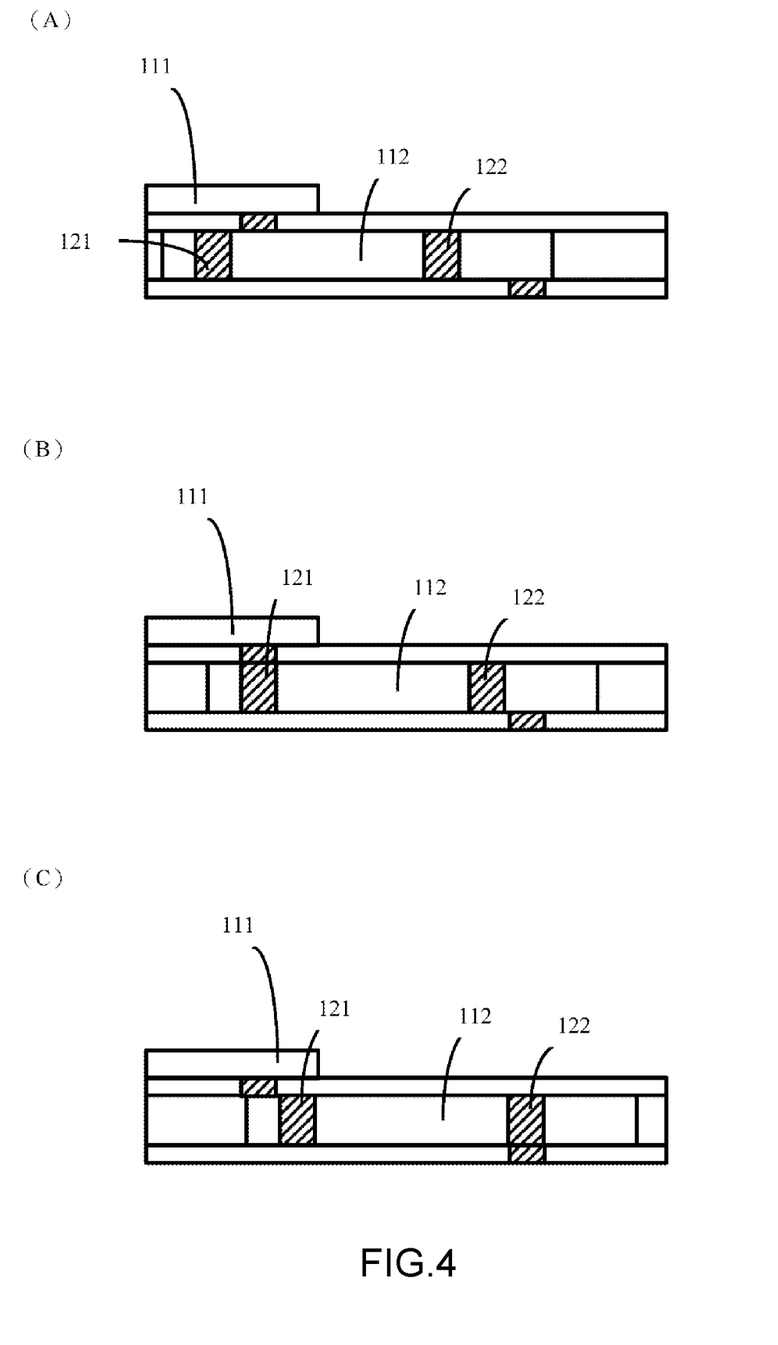
FIG. 4(A) to 4(C) are schematic views of how the centrifugal reaction microtube operates according to embodiment 3A of the present disclosure.

In embodiment 3A, as shown in FIG. 4, the centrifugal reaction microtube comprises a first reaction area 111, first uni-directional valve 121, second reaction area 112 and second uni-directional valve 122. Unlike embodiment 3, the difference is that the first uni-directional valve 121 and second uni-directional valve 122 are controlled by one single spring. As shown in FIG. 4(A), the first uni-directional valve 121, second reaction area 112 and second uni-directional valve 122 together form a sliding element which slides in the direction of the centrifugal force during centrifugation. Wherein the sliding element may be connected to a spring whereby the sliding element may return to a position of stationary state upon centrifugation. In a preferred embodiment, the spring may be a compression spring located on the right of the sliding element in the drawing. Alternatively, the spring may be an extension spring located on the left of the sliding element.

For instance, FIG. 4(A) shows the centrifugal reaction microtube has not yet undergone centrifugation, wherein the first reaction area 111 and second reaction area 112 are not in communication with each other, and the sliding element is at a first position of stationary state. When centrifugation is carried out under the first centrifugal force, the sliding element moves to the second position shown in FIG. 4(B). As a result, a through hole is in communication with the first uni-directional valve 121 to allow the reaction reagent, rinsing solution and/or specimen to move from the first reaction area 111 to the second reaction area 112 via the first uni-directional valve 121; meanwhile, the second uni-directional valve 122 has not yet been in communication with the through hole, and thus the reaction reagent, rinsing solution and/or specimen do not pass through the second uni-directional valve 122. When centrifugation is further carried out under the second centrifugal force which is greater than the first centrifugal force, the sliding element moves to the third position shown in FIG. 4(C). As a result, the through hole is in communication with the second uni-directional valve 122, but the through hole is not in communication with the first uni-directional valve 121, thereby allowing the reaction reagent, rinsing solution and/or specimen to leave from the second reaction area 112 via the second uni-directional valve 122 without flowing back to the first reaction area 111.

Figure 5:
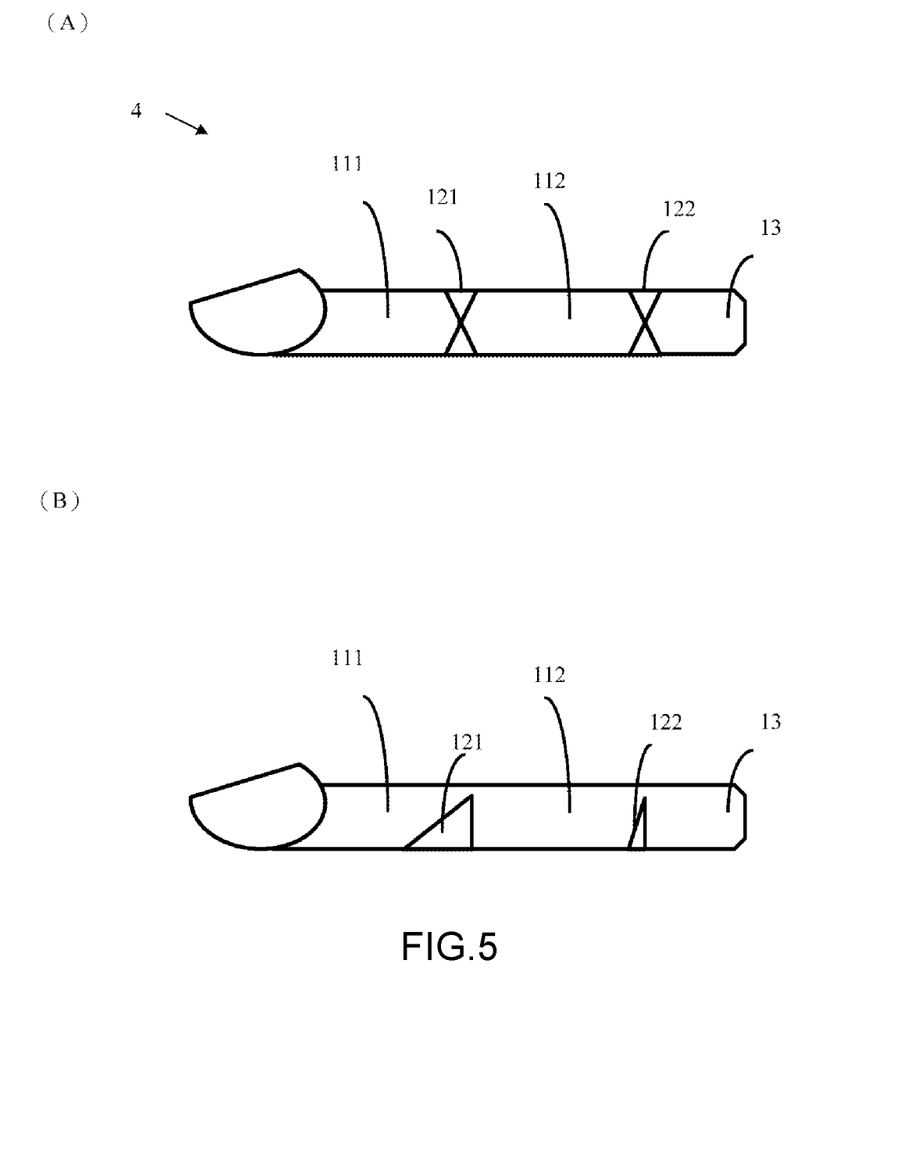
FIG. 5(A), 5(B) are schematic views of the centrifugal reaction microtube according to embodiments 4, 4A of the present disclosure.

In embodiment 4, as shown in FIG. 5(A), the centrifugal reaction microtube 4 not only comprises the first reaction area 111, first uni-directional valve 121, second reaction area 112 and second uni-directional valve 122 but also comprises the liquid waste area 13 for collecting a liquid waste after the reaction.

As shown in FIG. 5(B), unlike embodiment 4, embodiment 4A has distinguishing technical features as follows: the first uni-directional valve 121 and second uni-directional valve 122 in the centrifugal reaction microtube are oblique; and the slope of the second uni-directional valve 122 is greater than the slope of the first uni-directional valve 121. In this embodiment, before centrifugation, the reaction reagent, rinsing solution and/or specimen are separated by the first uni-directional valve 121 and thus stay in the first reaction area 111. Upon centrifugation under the first centrifugal force, the reaction reagent, rinsing solution and/or specimen move from the first reaction area 111 to the second reaction area 112 via the first uni-directional valve 121. Since the slope of the second uni-directional valve 122 is greater than the slope of the first uni-directional valve 121, the reaction reagent, rinsing solution and/or specimen do not pass through the second uni-directional valve 122. When centrifugation is further carried out under the second centrifugal force which is greater than the first centrifugal force, the reaction reagent, rinsing solution and/or specimen exit the second reaction area 112 pass through the second uni-directional valve 122 whose slope is relatively great, without flowing back to the first reaction area 111.

Figure 6:
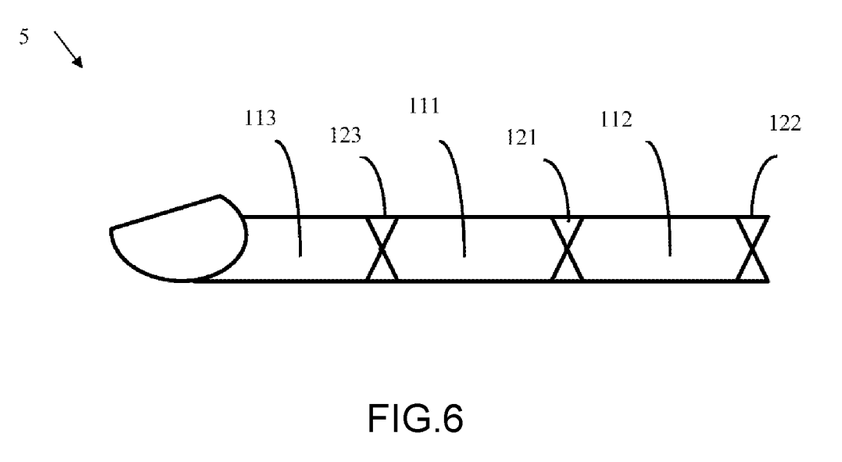
FIG. 6 is a schematic view of the centrifugal reaction microtube according to embodiment 5 of the present disclosure.

As shown in FIG. 6, embodiment 5 is similar to embodiment 3, but a centrifugal reaction microtube 5 not only comprises a first reaction area 111, first uni-directional valve 121, second reaction area 112 and second uni-directional valve 122 but also comprises a third reaction area 113 and a third uni-directional valve 123. The third reaction area 113 contains a reaction mixture for undergoing a third reaction. The third uni-directional valve 123 is disposed between the third reaction area 113 and the first reaction area 111. Under the third centrifugal force, the reaction mixture moves to the first reaction area 111.

In embodiment 5, given the three reaction areas, three reactions may be performed sequentially in the same centrifugal reaction microtube 5. For instance, the third reaction area 113 may undergo a nucleic acid extraction reaction, and the first reaction area 111 may undergo a polymerase chain reaction, and/or the second reaction area 112 may undergo nucleic acid hybridization.

In a preferred embodiment, as mentioned before, during centrifugation, to prevent the reaction mixture in the third reaction area 113 from passing through the first uni-directional valve 121, second uni-directional valve 122 and third uni-directional valve 123 without staying in the first reaction area 111, or prevent the reaction mixture in the first reaction area 111 from passing through the first uni-directional valve 121 and second uni-directional valve 122 simultaneously without staying in the second reaction area 112, it is feasible to select the second uni-directional valve 122, first uni-directional valve 121 and third uni-directional valve 123 sequentially according to the elastic moduli (in the order from great to small) of the uni-directional valves. Therefore, at the lowest rotation speed, only the third uni-directional valve 123 opens, but the first uni-directional valve 121 and second uni-directional valve 122 shut. At the rotation speed suitable for the first uni-directional valve 121 to open, the first uni-directional valve 121 and third uni-directional valve 123 open, but the second uni-directional valve 122 remains shut.

Figure 7:
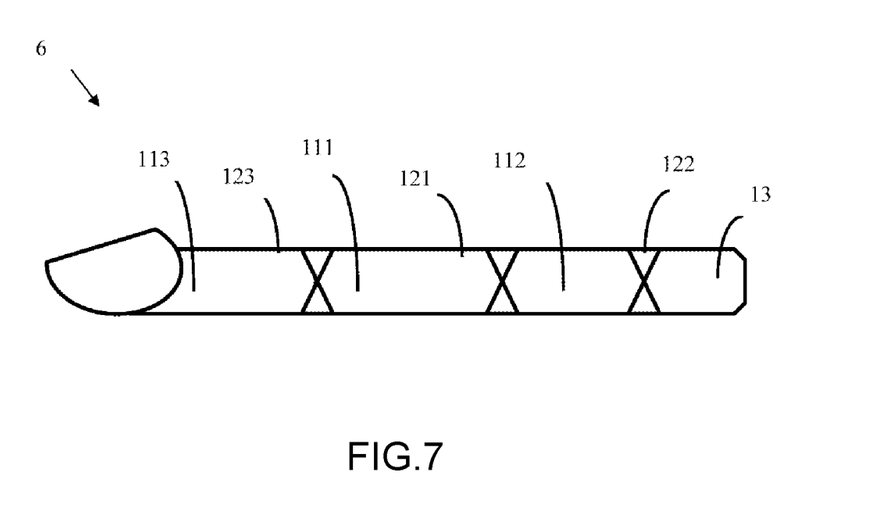
FIG. 7 is a schematic view of the centrifugal reaction microtube according to embodiment 6 of the present disclosure.

In embodiment 6, as shown in FIG. 7, a centrifugal reaction microtube 6 not only comprises the first reaction area 111, first uni-directional valve 121, second reaction area 112, second uni-directional valve 122, third reaction area 113 and third uni-directional valve 123 but also comprises a liquid waste area 13 for collecting a liquid waste after the reaction.

Since reactions, for example, polymerase chain reaction and nucleic acid hybridization, as well as performing qualitative and quantitative detection of products of reactions, have to be performed in the centrifugal reaction microtube, the centrifugal reaction microtube is preferably made of heat resisting optical materials. The term "heat resisting" means that the properties, for example, optical properties, of the centrifugal reaction microtube remain unchanged at a specific temperature. Preferably, the specific temperature is at least 120° C. The term "optical materials" means that the materials have characteristics, such as low chromatic dispersion, low chromatic aberration, broad range of wavelength of light penetration, low refractive index, and high transmittance. Preferably, the optical materials include quartz, glass or plastic.

Figure 8:
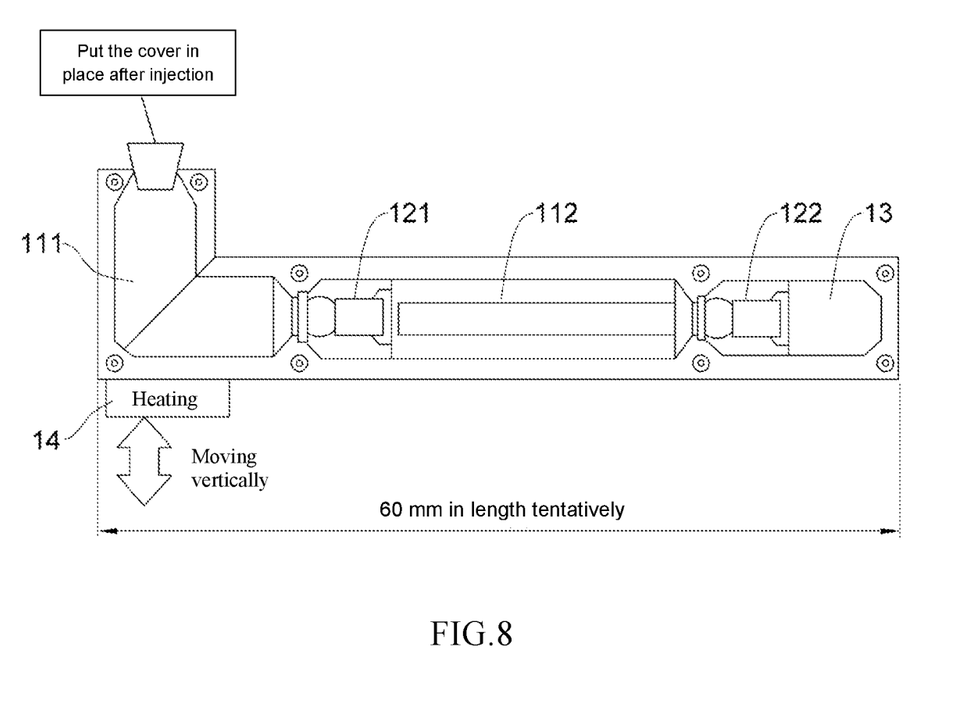
FIG. 8 is a schematic view of the centrifugal reaction microtube according to a preferred embodiment of the present disclosure.

In a preferred embodiment, providing a centrifugal reaction microtube. As shown in FIG. 8, the centrifugal reaction microtube comprises a first reaction area 111, first uni-directional valve 121, second reaction area 112, second uni-directional valve 122 and liquid waste area 13. After the reaction reagent or specimen has been added to the reaction microtube, the mouth of the reaction microtube may be sealed with a cover to prevent the reaction reagent or specimen from leaking out. The centrifugal reaction microtube may be 60 mm in length which, however, may be adjusted by persons skilled in the art as needed and according to the centrifugation device in use. For instance, when the centrifugal reaction microtube has, as disclosed in embodiment 1, only one reaction area and one uni-directional valve, the centrifugal reaction microtube may be 40 mm in length. Alternatively, when the centrifugal reaction microtube has, as disclosed in embodiment 5, three reaction areas and three uni-directional valves, the centrifugal reaction microtube may be 100 mm in length.

The outer edge of the first reaction area 111 may be adjacent to a heating module 14 whereby the temperature of the first reaction area 111 is increased by substantial contact heating. Preferably, the heating module 14 may be U-shaped in order to effectively surround the first reaction area 111, thereby increasing the speed of heating up the first reaction area 111. Similarly, a heating module may be disposed both outside the first reaction area 111 and second reaction area 112 to independently control the reaction temperature of the first reaction area 111 and second reaction area 112.

In an embodiment, the present disclosure provides a centrifugal reaction device, comprising a reaction centrifugal disk tilting upward at a slope from the axle. A plurality of holders are symmetrically disposed on the reaction centrifugal disk and adapted to receive a plurality of centrifugal reaction microtubes. Therefore, the reaction centrifugal disk is saucer-shaped (i.e., has a low center and a high edge) and tilts upward and outward from the axle. As a result, after being placed in the reaction centrifugal disk, the reaction microtubes tilt spontaneously, allowing liquid in the reaction microtubes to flow spontaneously toward the axle of the reaction centrifugal disk under the gravity. Thus, the larger the tilting angle of the reaction centrifugal disk is, the higher is the speed at which the reaction mixture flows back upon centrifugation to thereby speed up the reaction and save energy. At the end of the centrifugation or with the centrifugal force diminishing, the liquid thrown out by the centrifugation flows downward (i.e., flows back toward the axle of the reaction centrifugal disk) under the gravity. The intermittent centrifugation is conducive to quick exchange or mixing of liquid in the absence of any transfer equipment. Preferably, the slope, at which the reaction centrifugal disk tilts from the axle, may range from about 1° to 89°, preferably 10° to 80°, 20° to 70°, 30° to 60°, 40° to 50° or the like. Optionally, the reaction centrifugal disk may lie horizontally, provided that the reaction microtubes can tilt.

Figure 9:
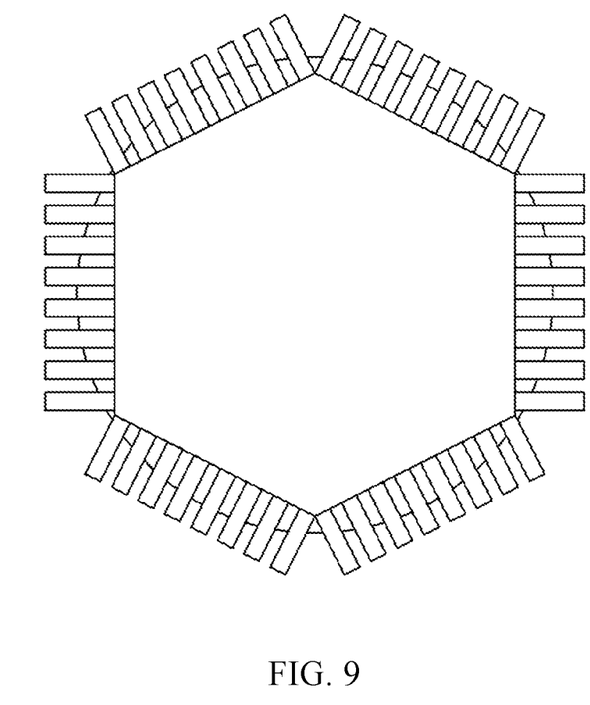
FIG. 9 is a schematic view of a reaction centrifugal disk according to an embodiment of the present disclosure.

In a preferred embodiment, to achieve high flux of reaction, every eight reaction microtubes disposed on the reaction centrifugal disk may be arranged in an array, as shown in FIG. 9, to speed up the introduction of the reaction reagent or specimen. However, FIG. 9 is not restrictive of the present disclosure, as the number of reaction microtubes arranged in an array is subject to changes as needed and according to the centrifugation device in use. For instance, the number of reaction microtubes arranged in an array may be 12, 8, 6, 4 or 2. Furthermore, as shown in FIG. 9, disposed on the reaction centrifugal disk are six groups of reaction microtubes, and each group consists of eight reaction microtubes arranged in an array. Likewise, the number of groups of reaction microtubes disposed on the reaction centrifugal disk is subject to changes as needed and according to the reaction centrifugal disk in use. For instance, the number of groups of reaction microtubes disposed on the reaction centrifugal disk may be 8, 6, 4 or 2.

In an embodiment, the centrifugal reaction device may further comprises a liquid dispenser for adding the reaction reagent and/or specimen to the centrifugal reaction microtubes. The mouth (for example, the left end of the centrifugal reaction microtube 1 shown in FIG. 1) of each centrifugal reaction microtube is disposed toward the axle of the reaction centrifugal disk, such that there is no need of large range movement for introducing reaction reagent and/or specimen of the liquid dispenser, which causes longer time.

In an embodiment, the centrifugal reaction device may further comprises a temperature controller for controlling the reaction temperature of the centrifugal reaction microtube, including heating blocks, liquid (such as hot water), gas (such as hot air), or far-infrared ray. Preferably, during the heating process, the heating blocks and liquid are arranged in a U-shaped or O-shaped to surround the centrifugal reaction microtube and thereby enhance the efficiency of temperature control.

For instance, when polymerase chain reaction is taking place in the reaction area, the temperature in the reaction area should be controlled and kept at 0° C.-100° C., preferably 4° C.-95° C. For instance, in a denaturing stage, the temperature in the reaction area is controlled and kept at 96° C. to denature double-stranded DNA; in a annealing stage, the temperature in the reaction area is controlled and kept below about 60° C. to attach the primer and template DNA; and, in an extending stage, the temperature in the reaction area is controlled and kept at 72° C. to extend DNA, and the aforesaid cycle is repeated several times.

In an embodiment, the centrifugal reaction device may further comprises a signal detector for detecting a reaction signal of the centrifugal reaction microtube. For instance, the signal detector may be a fluorescence, photoluminescence or visible light photography and sensing system. At the end of the reaction in the reaction area of the centrifugal reaction microtube, biological molecules (such as antibodies, aptamers, peptides or nucleic acids) of marker fluorescence, photoluminescence or color signals may be added to the reaction area to perform qualitative or quantitative analysis of the products of reaction through detecting the signals.

Preferably, the centrifugal reaction device may further comprises a liquid waste collector for collecting a liquid waste exiting the centrifugal reaction microtube. For instance, in embodiment 1, embodiment 3 and embodiment 5 of the centrifugal reaction microtube, none of the centrifugal reaction microtubes 1, 3, 5 has the liquid waste area 13, and thus it is impossible for the centrifugal reaction microtubes 1, 3, 5 to collect a reaction liquid waste. In this situation, a liquid waste collector is disposed in the centrifugal reaction device and adapted to collect a liquid waste exiting the centrifugal reaction microtubes. In a preferred embodiment, the liquid waste collector is a vacuum extraction device disposed on the inner wall of the centrifugal reaction device. When a liquid waste exits the centrifugal reaction microtubes 1, 3, 5 via a uni-directional valve, the liquid waste is extracted and removed by the vacuum extraction device without splashing back to the opened uni-directional valve to otherwise cause reaction contamination.

In yet an embodiment, the present disclosure provides a centrifugation examination method, comprising the steps of: providing a centrifugal reaction microtube; and adding a specimen and/or reaction reagent to a reaction area to form a reaction mixture, allowing the centrifugal reaction microtube to undergo centrifugation and thereby effectuate a reaction.

A centrifugation examination method provided according to an embodiment of the present disclosure is illustrated by FIG. 3 and explained below. First, a specimen and/or a reaction reagent are sequentially added to the centrifugal reaction microtube 3 to form a reaction mixture. The centrifugal reaction microtube 3 is centrifuged in order to undergo a first reaction in the first reaction area 111. The centrifugation speed or centrifugal force is controlled, such that the reaction mixture is sufficiently vibrated to undergo the first reaction while the first uni-directional valve 121 and second uni-directional valve 122 are shut. Then, the centrifugal reaction microtube 3 undergoes centrifugation under the first centrifugal force and at a speed corresponding thereto, such that the reaction mixture moves, via the opened first uni-directional valve 121, to the second reaction area 112 to undergo a second reaction. The centrifugal reaction microtube 3 undergoes centrifugation under the second centrifugal force and at a speed corresponding thereto, such that the reaction mixture exits the second reaction area 112 via the opened second uni-directional valve 122. Optionally, in the course of reaction, the liquid dispenser adds the rinsing solution to the centrifugal reaction microtube 3, and the centrifugal reaction microtube 3 undergoes centrifugation at the speed associated with a centrifugal force less than the first and second centrifugal forces to vibrate and rinse the first reaction area 111 or second reaction area 112.

Specific Embodiment of Centrifugation Examination Method (1) A nucleic acid specimen and a reaction reagent are added to the centrifugal reaction microtube with a liquid dispenser.
  I. 1-20 μL of specimen under test is taken out of a specimen chamber (such as 1.5 mL centrifuge tube or 96-well plate) and added to the centrifugal reaction microtube.
  II. 1-20 μL of reagent is taken out of a reagent chamber (such as 1.5 mL centrifuge tube) and added to the centrifugal reaction microtube.
  III. 20-30 μL of mineral oil is taken out of another reagent chamber (such as 1.5 mL or 15 mL centrifuge tube) and added to the centrifugal reaction microtube.
  IV. Centrifugation is carried out at low speed (under a centrifugal force of 10-100 g, for example) to mix the specimen and the reaction reagent in the first reaction area while the first uni-directional valve and the second uni-directional valve remain shut.

(2) Polymerase chain reaction is carried out in the first reaction area through centrifugation-induced mixing and temperature control to produce amplicons.

Polymerase chain reaction is carried out at 37-60-95° C. in about 40-45 reaction cycles.

(3) First signal detection and quantitative analysis of nucleic acids.

Nucleic acid concentration is detected with a spectrophotometer in the centrifugal reaction device.

(4) Centrifugation is carried out under the first centrifugal force to allow amplicons to enter the second reaction area containing a nucleic acid biochip via the first uni-directional valve.
  I. Preheat the second reaction area to 50-60° C.
  II. 20 μL of denaturing solution (strong base) is taken out of a reagent chamber (such as 1.5 mL or 15 mL centrifuge tube) and added to the centrifugal reaction microtube.
  III. Centrifugation is carried out at low speed (under a centrifugal force of 10-100 g, for example) to allow the denaturing solution to pass through the mineral oil and mix with the original reaction mixture; meanwhile, the first uni-directional valve and second uni-directional valve remain shut.
  IV. Let the resultant reaction mixture stand still for 30 minutes to effectuate DNA denaturation and thus denature double-stranded DNA into single-stranded
  V. 100 μL of hybridization buffer solution (salt buffer solution) is taken out of the reagent chamber (such as 1.5 mL or 15 mL centrifuge tube) and added to the centrifugal reaction microtube.
  VI. Centrifugation is carried out at low speed (under a centrifugal force of 10-100 g, for example) to allow the hybridization buffer solution and the reaction mixture to mix within the first reaction area and facilitate hybridization; meanwhile, both the first uni-directional valve and second uni-directional valve remain shut.
  VII. Centrifugation is carried out at medium speed (under a centrifugal force of 500-1000 g, for example) to open the first uni-directional valve only and move the aforesaid mixture from the first reaction area to the second reaction area.

(5) Nucleic acid hybridization takes place in the second reaction area through centrifugation-induced mixing and temperature control and rinsing step takes place.
  I. Centrifugation is carried out intermittently at low speed (under a centrifugal force of 10-100 g, for example) at a specific temperature (for example, 50° C.) for a specific time period (for example, 30-60 min) to allow the reaction mixture to undergo reciprocating motion under a centrifugal force and the gravity, within the second reaction area, so as to facilitate hybridization.
  II. Centrifugation is carried out at high speed (under a centrifugal force of 1500-4000 g, for example) to open the second uni-directional valve and thus move the entire reaction mixture from the second reaction area to the liquid waste area or the liquid waste collector of the centrifugal reaction device.
  III. 100 μL of rinsing solution 1 (salt buffer solution) is taken out of the reagent chamber (such as 1.5 mL or 15 mL centrifuge tube) and added to the centrifugal reaction microtube to undergo centrifugation at medium speed (under a centrifugal force of 500-1000 g, for example) to open the first uni-directional valve only and move the rinsing solution 1 to the second reaction area. Then, the biochip is rinsed by centrifugation intermittently at low speed (under a centrifugal force of 10-100 g, for example) for 3 minutes.

IV. Centrifugation is carried out at high speed (under a centrifugal force of 1500-4000 g, for example) to open the second uni-directional valve and thus remove the rinsing solution 1 from the second reaction area.

V. 100 μL of rinsing solution 2 (salt buffer solution) is taken out of the reagent chamber (such as 1.5 mL or 15 mL centrifuge tube) and added to the centrifugal reaction microtube. Centrifugation is carried out at medium speed (under a centrifugal force of 500-1000 g, for example) to open the first uni-directional valve only and move the rinsing solution 2 to the second reaction area. Then, the biochip is rinsed by centrifugation intermittently at low speed (under a centrifugal force of 10-100 g, for example) for 3 minutes.

VI. Centrifugation is carried out at high speed (under a centrifugal force of 1500-4000 g, for example) to open the second uni-directional valve and remove the rinsing solution 2 from the second reaction area.

(6) Second signal interpretation and qualitative analysis of nucleic acids

I. 50 μL of an antibody-containing conjugate solution (salt buffer solution) is taken out of the reagent chamber (such as 1.5 mL or 15 mL centrifuge tube) and added to the centrifugal reaction microtube. Centrifugation is carried out at medium speed (under a centrifugal force of 500-1000 g, for example) to open the first uni-directional valve only and move the conjugate solution to the second reaction area. Then, centrifugation is carried out intermittently at low speed (under a centrifugal force of 10-100 g, for example) to allow the conjugate solution to react with the biochip for 20 minutes.

II. Centrifugation is carried out at high speed (under a centrifugal force of 1500-4000 g, for example) to open the second uni-directional valve and remove the conjugate solution from the second reaction area.

III. 100 μL of rinsing solution 3 (salt buffer solution) is taken out of the reagent chamber (such as 1.5 mL or 15 mL centrifuge tube) and added to the centrifugal reaction microtube. Centrifugation is carried out at medium speed (under a centrifugal force of 500-1000 g, for example) to open the first uni-directional valve only and move the rinsing solution 3 to the second reaction area. Then, the biochip is rinsed by centrifugation intermittently at low speed (under a centrifugal force of 10-100 g, for example) for 3 minutes.

IV. Centrifugation is carried out at high speed (under a centrifugal force of 1500-4000 g, for example) to open the second uni-directional valve and remove the rinsing solution 3 from the second reaction area.

V. 50 μL of coloring agent (salt buffer solution) is taken out of the reagent chamber (such as 1.5 mL or 15 mL centrifuge tube) and added to the centrifugal reaction microtube. Centrifugation is carried out at medium speed (under a centrifugal force of 500-1000 g, for example) to open the first uni-directional valve only and move the coloring agent to the second reaction area. Then, centrifugation is carried out intermittently at low speed (under a centrifugal force of 10-100 g, for example) to allow the coloring agent to react with the biochip for 15 minutes.

VI. Centrifugation is carried out at high speed (under a centrifugal force of 1500-4000 g, for example) to open the second uni-directional valve and remove the coloring agent from the second reaction area.

VII. 100 μL of rinsing solution 4 (salt buffer solution) is taken out of the reagent chamber (such as 1.5 mL or 15 mL centrifuge tube) and added to the centrifugal reaction microtube. Centrifugation is carried out at medium speed (under a centrifugal force of 500-1000 g, for example) to open the first uni-directional valve only and move the rinsing solution 4 to the second reaction area. Then, the biochip is rinsed by centrifugation intermittently at low speed (under a centrifugal force of 10-100 g, for example) for 3 minutes.

VIII. Centrifugation is carried out at high speed (under a centrifugal force of 1500-4000 g, for example) to open the second uni-directional valve and remove the rinsing solution 4 from the second reaction area.

IX. 100 μL of fixation termination agent (salt buffer solution) is taken out of the reagent chamber (such as 1.5 mL or 15 mL centrifuge tube) and added to the centrifugal reaction microtube. Centrifugation is carried out at medium speed (under a centrifugal force of 500-1000 g, for example) to open the first uni-directional valve only and move the fixation termination agent to the second reaction area. Then, centrifugation is carried out intermittently at low speed (under a centrifugal force of 10-100 g, for example) to allow the fixation termination agent to react with the biochip for 3 minutes.

X. Centrifugation is carried out at high speed (under a centrifugal force of 1500-4000 g, for example) to open the second uni-directional valve and remove the fixation termination agent from the second reaction area.

XI. 100 μL of rinsing solution 5 (salt buffer solution) is taken out of the reagent chamber (such as 1.5 mL or 15 mL centrifuge tube) and added to the centrifugal reaction microtube. Centrifugation is carried out at medium speed (under a centrifugal force of 500-1000 g, for example) to open the first uni-directional valve only and move the rinsing solution 5 to the second reaction area. Then, the biochip is rinsed by centrifugation intermittently at low speed (under a centrifugal force of 10-100 g, for example) for 3 minutes.

XII. Centrifugation is carried out at high speed (under a centrifugal force of 1500-4000 g, for example) to open the second uni-directional valve and remove the rinsing solution 5 from the second reaction area.

XIII. Pictures are sequentially taken with a camera according to specimen reference numbers on the biochip and then analyzed with software, and in consequence a result report is outputted. For instance, a specific point on a biochip corresponding to a specific patient's specimen undergoes a specific test and manifests a resultant color change, indicating that the specific patient yields positive test result.

(7) Examination is completed.

Therefore, the present disclosure provides a centrifugal reaction microtube, a centrifugal reaction device and its centrifugal examination method to achieve molecular biological testing with one click without human intervention. A size of molecular biological testing machine can be miniaturized with the centrifugal reaction microtube under a centrifugal force to save energy, save space and shorten testing duration. Furthermore, throughout its course, the reaction need not be switched between different machines, so as to render operation simple, quick, precise and cost-effective, ensure safety, save energy, and prevent contamination.

Although the present disclosure is disclosed above by preferred embodiments, the preferred embodiments are illustrative rather than restrictive of the present disclosure. Equivalent amendments or changes made by persons skilled in the art to the preferred embodiments without departing from the scope and spirit of the present disclosure must be deemed falling within the scope of the claims of the present disclosure.

What is claimed is:

1. A centrifugal reaction microtube comprising:
a first reaction space for containing a reaction mixture and for the reaction mixture to undergo a first reaction, the first reaction space including a first end and a second end;
a first unidirectional valve located in the second end and configured to enable the reaction mixture in the first reaction space to exit through the second end by transitioning from a first unidirectional valve closed state to a first unidirectional valve open state in response to application of a first centrifugal force; and
a second reaction space separated from the first reaction space by the first unidirectional valve, the second reaction space having a third end and a fourth end, wherein the first unidirectional valve is configured to enable the reaction mixture to move into the second reaction space in the first unidirectional valve open state under the first centrifugal force and undergo a second reaction; and
a second unidirectional valve disposed in the fourth end and configured to enable the reaction mixture in the second reaction space to exit through the fourth end by transitioning from a second unidirectional closed state to a second unidirectional open state in response to application of a second centrifugal force wherein the second reaction space is disposed radially outward in a centrifugation direction relative to the first reaction space and wherein the second centrifugal force is greater than the first centrifugal force.

2. The centrifugal reaction microtube of claim 1 wherein the first centrifugal force is between 1 g and 80,000 g and the second centrifugal force is between 1 g and 80,000 g.

3. The centrifugal reaction microtube of claim 1 further comprising a biochip disposed in the second reaction space and coated with one or more biological molecules including an antibody, an aptamer, a peptide or a nucleic acid.

4. The centrifugal reaction microtube of claim 1 further comprising a liquid waste area separated from the second reaction space by the second unidirectional valve.

5. The centrifugal reaction microtube of claim 1 wherein the first reaction space can contain one or more polymerase chain reaction reagents to undergo undergoes a polymerase chain reaction in the first reaction space.

6. The centrifugal reaction microtube of claim 5 wherein the second reaction space can contain one or more nucleic acid hybridization reagents to undergo a nucleic acid hybridization reaction in the second reaction space.

7. The centrifugal reaction microtube of claim 1 further comprising:
a third reaction space for containing the reaction mixture and for the reaction mixture to undergo a third reaction, the third reaction space including a fifth end and a sixth end;
a fourth space; and
a third unidirectional valve disposed in the sixth end and configured to enable the reaction mixture in the third reaction space to exit through the sixth end by transitioning from a third unidirectional closed state to a third unidirectional open state as a result of application of a third centrifugal force.

8. The centrifugal reaction microtube of claim 1 comprising an optical material having one or more optical properties.

9. The centrifugal reaction microtube of claim 8 wherein the optical material includes quartz, glass or plastic.

10. A centrifugal reaction device comprising:
a plurality of centrifugal reaction microtubes of the centrifugal reaction microtube of claim 1;
a reaction centrifugal disk configured to tilt upward at a slope from an axle and having a plurality of holders arranged symmetrically and adapted to receive the plurality of centrifugal reaction microtubes.

11. The centrifugal reaction device of claim 10 wherein the slope is between 1 and 89°.

12. The centrifugal reaction device of claim 10 further comprising:
a signal detector for detecting a reaction signal originating from the plurality of centrifugal reaction microtubes.

13. The centrifugal reaction device of claim 10 further comprising:
a liquid dispenser for introducing a reaction reagent or for introducing a specimen or for introducing both the reaction reagent and the specimen into the centrifugal reaction microtubes.

14. The centrifugal reaction device of claim 10 further comprising:
a temperature controller for controlling a reaction temperature of the plurality of centrifugal reaction microtubes.

15. The centrifugal reaction device of claim 10 further comprising a liquid waste collector for collecting a liquid waste originating from the plurality of centrifugal reaction microtubes.

16. A centrifugation examination method comprising:
providing the centrifugal reaction microtube of claim 1;
inducing a first reaction in the first reaction space by forming a reaction mixture by introducing a specimen or by introducing a reaction reagent or by introducing the specimen and the reaction reagent into the first reaction space; and centrifuging the centrifugal reaction microtube for a first time period.

17. The method of claim 16 further comprising:
introducing a rinsing solution into the centrifugal reaction microtube; intermittently centrifuging the centrifugal reaction microtube for a second time period.

18. The method of claim 16 further comprising:
detecting a reaction signal originating from the centrifugal reaction microtube.

19. The method of claim 16 further comprising:
controlling a reaction temperature of the centrifugal reaction microtube.

20. The method of claim 16 further comprising:
collecting a liquid waste from the centrifugal reaction microtube.

21. The method of claim 16 further comprising:
inducing a second reaction in the second reaction space by moving the reaction mixture through the first unidirectional valve to the second reaction space by centrifuging the centrifugal reaction microtube at the first centrifugal force.

22. The method of claim 21 further comprising:
moving the reaction mixture out of the second reaction space and through the second unidirectional valve by centrifuging the centrifugal reaction microtube at the second centrifugal force.

23. The method of claim 22 wherein the first centrifugal force is between 1 g and 80,000 g and the second centrifugal force is between 1 g and 80,000 g.

24. The method of claim 21 wherein the first reaction is a polymerase chain reaction.

25. The method of claim 24 wherein the second reaction is a nucleic acid hybridization reaction.

* * * * *